(12) United States Patent
Gagnon et al.

(10) Patent No.: US 8,073,109 B2
(45) Date of Patent: Dec. 6, 2011

(54) METHOD AND SYSTEM FOR PET IMAGE RECONSTRUCTION USING A SUROGATE IMAGE

(75) Inventors: Daniel Gagnon, Twinsburg, OH (US); Wenli Wang, Aurora, OH (US); Zhiqiang Hu, Highland Heights, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 914 days.

(21) Appl. No.: 12/088,090

(22) PCT Filed: Sep. 14, 2006

(86) PCT No.: PCT/IB2006/053287
§ 371 (c)(1), (2), (4) Date: Mar. 26, 2008

(87) PCT Pub. No.: WO2007/039841
PCT Pub. Date: Apr. 12, 2007

(65) Prior Publication Data
US 2008/0253640 A1 Oct. 16, 2008

Related U.S. Application Data

(60) Provisional application No. 60/596,587, filed on Oct. 5, 2005.

(51) Int. Cl.
*G06K 9/00* (2006.01)
(52) U.S. Cl. ............... 378/131; 250/363.02; 250/363.04
(58) Field of Classification Search .................. 382/131; 250/363.02–363.04
See application file for complete search history.

(56) References Cited

U.S. PATENT DOCUMENTS

| | | | | |
|---|---|---|---|---|
| 5,210,421 A * | 5/1993 | Gullberg et al. | ......... | 250/363.04 |
| 5,338,936 A * | 8/1994 | Gullberg et al. | ......... | 250/363.04 |
| 5,376,795 A * | 12/1994 | Hasegawa et al. | ....... | 250/363.04 |
| 5,565,684 A * | 10/1996 | Gullberg et al. | ......... | 250/363.04 |
| 6,661,865 B1 * | 12/2003 | Popilock | ........................ | 378/19 |
| 7,057,178 B1 * | 6/2006 | Manjeshwar et al. | ... | 250/363.04 |
| 2003/0004405 A1 * | 1/2003 | Townsend et al. | ............ | 600/407 |
| 2004/0167398 A1 | 8/2004 | Flohr et al. | | |
| 2004/0260176 A1 * | 12/2004 | Wollenweber et al. | ....... | 600/427 |
| 2005/0129295 A1 | 6/2005 | Shanmugam et al. | | |
| 2006/0097175 A1 * | 5/2006 | Ganin et al. | ............. | 250/363.03 |
| 2006/0163485 A1 | 7/2006 | Stearns et al. | | |
| 2008/0107229 A1 * | 5/2008 | Thomas et al. | .................... | 378/4 |
| 2009/0257633 A1 * | 10/2009 | Cook | ............................. | 382/131 |

OTHER PUBLICATIONS

Wang et al., Systematic and Distributed Time-of-Flight List Mode PET Reconstruction, IEEE Nuclear Science Symposium Conference Record, 2006, pp. 1715-1722.*

(Continued)

*Primary Examiner* — Alexander H Taningco

(57) ABSTRACT

A method and system for use in positron emission tomography, wherein a first processor element (234) is configured to reconstruct a plurality of positron annihilation events detected during a positron emission tomography scan using a list-based reconstruction technique to generate first volumetric data. A second reconstructor (226) is configured to reconstruct the plurality of events using a second reconstruction technique to generate second volumetric data for determining an error correction (228), the error correction applied to the first volumetric data to generate corrected volumetric data for generating a human-readable image (234). In one embodiment a multiplicative error correction is performed on the plurality of events, the first processor element (234) reconstructing the corrected plurality of events; and the second volumetric data error correction comprises an additive error correction.

18 Claims, 2 Drawing Sheets

OTHER PUBLICATIONS

Bai, C., et al.; CT-based attenuation correction in PET image reconstruction for the Gemini system; 2004; IEEE Trans. on Nuclear Science Symposium; vol. 5:3082-3086.

Cheng, J-C., et al.; Implementation of scatter corrected List-Mode OP-EM reconstruction algorithm and a dual (Histogram/List-Mode) reconstruction scheme for dynamic PET imaging; 2005; IEEE Trans. on Nuclear Science Symposium; pp. 2291-2295.

Conti, M., et al.; Implementation of Time-of-Flight on CPS HiRez PET scanner; 2004; IEEE Nuclear Science Symposium; pp. 2796-2800.

Eriksson, L., et al.; The ECAT HRRT: NEMA NEC evaluation of the HRRT system, the new high-resolution research tomograph; 2002; IEEE Trans on Nuclear Science; 49(5)2085-2088.

Kinahan, P. E., et al.; Attenuation correction for a combined 3D PET/CT scanner; 1998; Med. Phys.; 25(10) 2046-2053.

Moses, W. W.; Time of Flight in PET Revisited; 2003; IEEE Trans. on Nuclear Science; 50(5)1325-1330.

Rahmim, A., et al.; Statistical list-mode image reconstruction for the high resolution research tomograph; 2004; Phys. Med. Biol.; 49:4239-4258.

* cited by examiner

METHOD AND SYSTEM FOR PET IMAGE RECONSTRUCTION USING A SUROGATE IMAGE

CROSS REFERENCE TO RELATED APPLICATIONS

This application claims the benefit of U.S. provisional application serial no. 60/596,587 filed Oct. 5, 2005, which is incorporated herein by reference.

The present invention relates to the field of positron imaging, and more particularly to the reconstruction of data acquired in positron emission tomography (PET).

Positron emission tomography (PET) is a branch of nuclear medicine in which a positron-emitting radiopharmaceutical such as 18F-fluorodeoxyglucose (FDG) is introduced into the body of a patient. As the radiopharmaceutical decays, positrons are generated. More specifically, each of a plurality of positrons reacts with an electron in what is known as a positron annihilation event, thereby generating a coincident pair of 511 keV gamma rays which travel substantially in opposite directions along a line of coincidence. A gamma ray pair detected within a coincidence time is ordinarily recorded by the PET scanner as an annihilation event. In time of flight ("TOF") imaging, the time within the coincidence interval at which each gamma ray in the coincident pair is detected is measured. The time of flight information provides an indication of the location of the detected event along the line of coincidence. Data from a plurality of annihilation events is used to reconstruct or create images of the patient or object scanned, typically by using statistical (iterative) or analytical reconstruction algorithms. More particularly, the reconstructed images provide information about the distribution of the radionuclide in the object.

To improve the fidelity of the resultant image, various error corrections are applied in connection with the reconstruction process. These corrections include, for example, scanner-specific corrections based on the characteristics of the scanner and object-specific corrections based on the composition of the patient or other object being examined.

While TOF information has proven to be useful, it has increased the complexity of the reconstruction process. In particular, histogram-based reconstruction algorithms are relatively inefficient in their handling of the TOF data. If the rebinning operation associated with histogram-based approaches bins an event occurring anywhere on a given line of coincidence in a single bin, the time of flight information is lost. While additional bins can be created to account for the time of flight information, doing so requires additional memory and increases processing time.

Event-by-event or list mode reconstruction techniques, on the other hand, can more readily accommodate the TOF information. However, it can be difficult to apply necessary corrections on an event-by-event basis. For example, certain implementations of corrections require preliminary knowledge of the object being examined to evaluate the distribution and amount of correction. Applying these corrections can thus lead to inefficiencies in the reconstruction process, and thus increase processing time.

The present invention provides a method and system for use in positron emission tomography, wherein a first processor element is configured to reconstruct a plurality of positron annihilation events detected during a positron emission tomography scan using a list-based reconstruction technique to generate first volumetric data. A second reconstructor is configured to reconstruct the plurality of events using a second reconstruction technique to generate second volumetric data for determining an error correction. The error correction is applied to the first volumetric data to generate corrected volumetric data for generating a human-readable image.

In one aspect of the invention the plurality of detected annihilation events is rebinned, and the second reconstructor reconstructs the rebinned data. In another aspect of the invention the second reconstructor uses a list-based reconstruction technique to reconstruct a subset of the plurality of detected events.

In another aspect of the invention a multiplicative error correction is performed on the plurality of events, the first processor element generating the first volumetric data by reconstructing the corrected plurality of events; and the second volumetric data error correction comprises an additive error correction including at least one of scatter and randoms.

Figure 1:
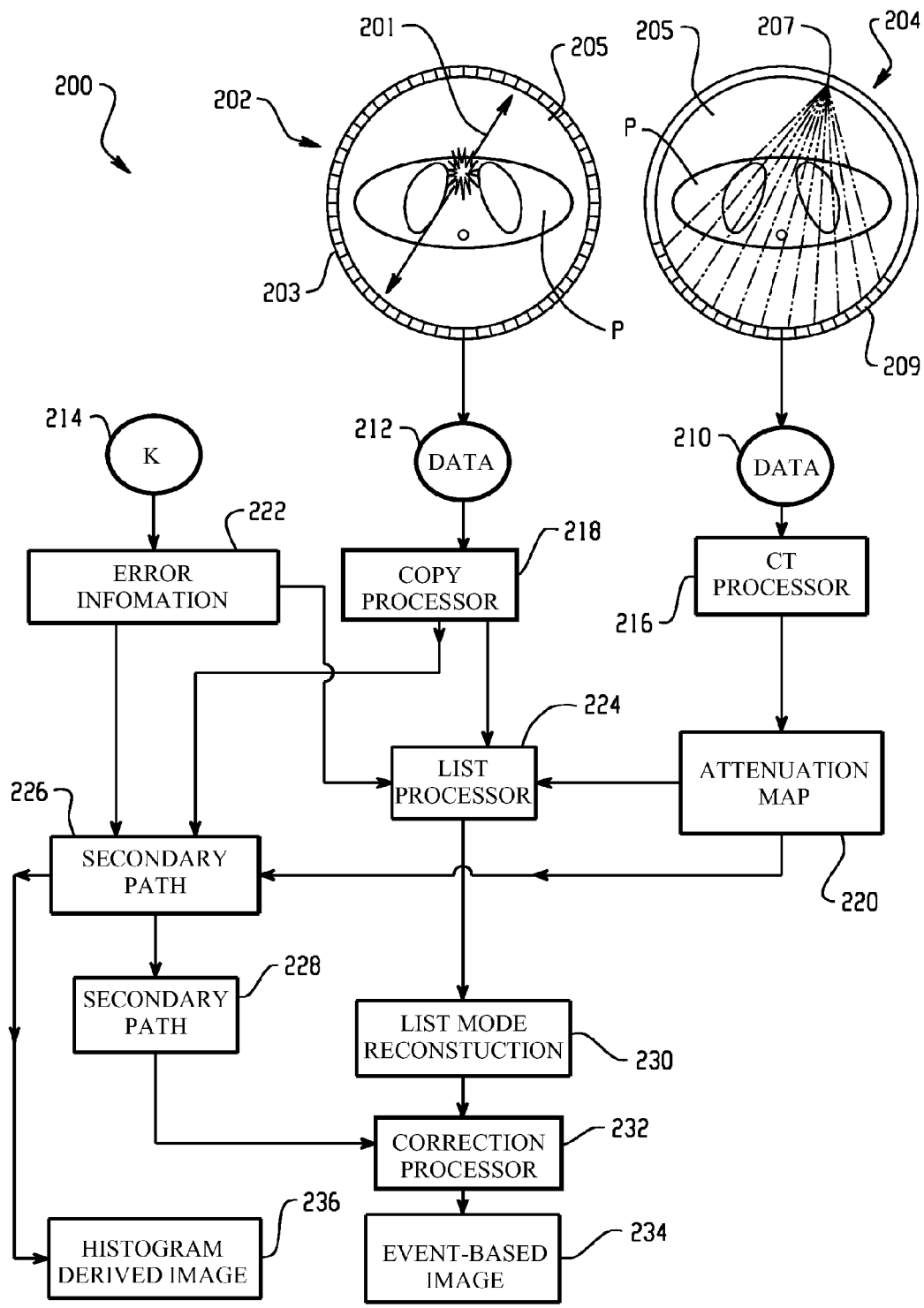
FIG. 1 illustrates a technique for reconstructing PET images.

Error correction is ordinarily a component of positron emission tomography (PET) image reconstruction. Main error correction categories include normalization, attenuation, randoms, and scatter.

A histogram-based maximum likelihood expectation maximization ("MLEM") reconstruction framework can be expressed by the following set of equations, wherein it is assumed that measured list-mode data is binned into sinogram form as according to an appropriate coordinate system, for example (r, phi, slc, l) or (s, z, phi, theta, l).

$$\bar{g}_j = \eta_j^{xtaleff} \eta_j^{decay} \eta_j^{deadtime} \left( \eta_j^{detgeon} \eta_j^{atten} \sum_i H_{ji} f_i + sc_j(f, \mu) + r_j \right) \quad \text{Equation A}$$

$$\text{where } H_{ji} = H_{ji}^{objRayWeight} H_{ji}^{TOF}$$

Following reconstruction, the resulting image can be expressed as follows:

$$\hat{f}_i^{k+1} = \frac{\hat{f}_i^k}{s_i} \sum_{j=0}^{J-1} \eta_j^{multi} \eta_j^{detgeom} \eta_j^{atten} H_{ji}^{objRayWeight} H_{jn}^{TOF} \quad \text{Equation B}$$

$$\frac{g_j^{Measured}}{\eta_j^{multi} \left( \eta_j^{degeom} \eta_j^{atten} \sum_{n=0}^{N-1} H_{jn}^{objRayWeight} \atop H_{jn}^{TOF} \hat{f}_n^k + sc(\hat{f}^k)_j + r_j \right)}$$

$$= \frac{\hat{f}_i^k}{s_i} \sum_{j=0}^{J-1} H_{ji}^{objRayWeight} H_{ji}^{TOF}$$

$$\frac{1}{\sum_{n=0}^{N-1} H_{jn}^{objRayWeight} H_{jn}^{TOF} \hat{f}_n^k + \frac{r_j + sc(\hat{f}^k)_j}{\eta_j^{detgeom} \eta_j^{atten}}} \quad \text{where}$$

$$\eta_j^{multi} = \eta_j^{xtaleff} \eta_j^{decay} \eta_j^{deadtime}$$

$$s_i = \sum_{\text{all possible } j} \eta_j^{multi} \eta_j^{detgeon} \eta_j^{atten} H_{ji}^{objRayWeight}$$

In the above equations, index j indicates a projection data bin (s, z, phi, theta, l) and index i indicates an object bin (x, y, z) or (u, v, w).

As reflected by the above equations, PET scanner image reconstruction errors may be categorized as either additive or multiplicative. Multiplicative error corrections include normalization and attenuation corrections (e.g., $\eta_j^{atten}$, $\eta_j^{degeom}$, $\eta_j^{decay}$ and $\eta_j^{deadtime}$). Additive corrections include scatter (sc) and randoms (r).

While the above equations focus on re-binned or histogram based reconstruction techniques, it is possible to convert the problem so that the events are reconstructed and corrected on an event-by-event basis. An event-based image reconstruction would be identical to that described above in Equation B except that the measured data $g_j^{Measured}$ is replaced by the number 1 to signify one event, and j then signifies the event number. Alternatively, event-based reconstruction can also be applied to histogram binned data by repeating the 1 sum proportionally to the number of events accumulated in a particular pixel ($g_j$) and repeating the process for each pixel.

The use of an event-by-event reconstruction is attractive from an information flow point of view if a pipeline operation from detection to final image can be defined. However, incorporating the additive corrections (e.g., scatter and randoms) requires breaking the flow, as preliminary knowledge of the object is required to evaluation the distribution and amount of correction. Accordingly it would be desirable to apply the additive corrections while maintaining an efficient data flow.

Turning now to FIG. 1, a PET scanner 202 includes one or more rings of radiation sensitive detectors 203 disposed about an examination region 205. The PET scanner generates event-by-event or list mode data 212 indicative of a plurality of positron annihilation events occurring within a patient or other object disposed in the examination region 205. This data 212 includes information describing the line of coincidence along which each event occurred, as well as TOF information which allows the location of the event along the line of coincidence to be estimated. While classical PET data 212 does not include TOF data, it will be apparent to one skilled in the art that TOF data may be added.

A CT scanner 204 provides information indicative of the radiation attenuation of a patient or other object disposed in its examination region 207. The CT scanner 204 includes a radiation source such as an x-ray tube which rotates about the scanner's examination region 207. Radiation passing through the examination region is detected by an arc or ring of radiation sensitive detectors 209 which provides CT data 210 information indicative of the radiation attenuation along a plurality of lines or rays.

The PET and CT scanners are preferably located in proximity to one another with their imaging regions 205, 207 aligned a common longitudinal or z-axis. The scanners also share a common patient support. In operation, the patient support is translated in the longitudinal direction so that the patient is received in the examination region 205, 207 of each scanner 202, 204.

While the radiation attenuation information has been described as being provided by a CT scanner 204, other techniques for obtaining attenuation information may be implemented. For example, the PET scanner may include a radiation source which emits radiation which traverses the examination region 205 of the PET scanner 202.

Constants K 214 comprise known scanner specific corrections based on PET scanner system performance parameters. Examples include the coefficients related to, detector crystal efficiency ($\eta_j^{xtaleff}$), normalization ($\eta_j^{atten}$), detector geometry ($\eta_j^{degeom}$), detector crystal decay time ($\eta_j^{decay}$), dead time $\eta_j^{deadtime}$ constants, and the like, in connection with Equations A and B as described above. For example, observing that an individual PET detector 203 is not operational or has lost some sensitivity may result in a constant performance modifier K 214 to be applied to detection data reported by that detector 203.

A CT processor 216 reconstructs the data 210 generated by the CT scanner to generate information indicative of the radiation attenuation of the object being examined in a volumetric or image space. The attenuation information is generally expressed in Hounsfield Units (HU). As the CT scanner 202 typically provides image data having a resolution higher than that provided by the PET scanner 202, the image data may be rescaled to match the resolution of the image data to be produced by the PET scanner. The tomographic or volumetric data is further processed to generate an attenuation map indicative 220 of the object being examined. Information from the attenuation map is used to correct for errors resulting from non-uniform radiation attenuation characteristics of the object being examined (e.g., the presence of bones in a human patient). It should be appreciated that the invention is not limited to use of CT data from a CT scanner, but may also include other types of data, such as, for example, transmission data, ultrasound data or magnetic resonance data, from respective scanner sources.

The PET data 212 is received by a copy processor 218, which generates data for use by a secondary proxy processing path 226/228. In one embodiment, the copy processor 218 rebins the PET data 212 for reconstruction using a histogram based technique, as is described below; more particularly, the data may be rebinned into a relatively smaller number of bins, for example by disregarding the TOF information contained in the list mode data. In any case, the list mode data 212 is also preserved for use by the list processor 224.

As noted above, attenuation correction is generally applied in PET image reconstruction to achieve count values independent from object tissue densities. The list processor 224 applies the attenuation correction and other desired multiplicative corrections to each event in the PET data 212. More particularly, the list processor applies multiplicative corrections based on the attenuation map 220 and scanner-specific sensitivity and normalization information 222 utilizing the equations described above. Where each event in the list mode PET data 212 has a unity initial weighting, the list processor 224 assigns a weight to each event based on the multiplicative correction factors, illustratively including the scanner-specific error information 222 and the attenuation coefficient information 220. However, the additive corrections (e.g., those necessary to correct for scatters and randoms) are not applied.

The re-weighted data from the list processor 224 is received by a list mode reconstructor 230, which reconstructs the data to provide volumetric data in image space, preferably using the MLEM technique described above, although other reconstruction algorithms could also be used.

Thus, the reconstructed image includes the multiplicative error corrections (e.g., sensitivity, normalization and attenuation error correction). As will be appreciated, the image as reconstructed by the list mode reconstructor 230 does not include the additive corrections (e.g., scatters and randoms).

The Additive error corrections such as scatter generally address low frequency errors, such that a high degree of spatial resolution is not essential. Moreover, processing efficiencies may be achieved if the additive error corrections are performed in image space, rather than to each individual event, since the additive error corrections may instead be applied to a relatively smaller number of voxels of image space rather than the generally much lesser number of events comprising the PET list mode data 212. Additionally, further time efficiencies may be provided by accomplished by providing a secondary processing path 226/228 to produce proxy image correction information 228 in parallel with the primary processing path 224/230.

Where the secondary processing path 226/228 provides a faster image reconstruction process relative to the primary processing path 224/230, then the proxy image correction 228 may be completed and provided in advance of the completion of the primary processing path image space reconstruction 230, so that the image space proxy image correction 228 is available before it is needed by the slower parallel primary list processing path 224/230. However, either one of the primary processing path list mode image reconstruction 230 and the secondary processing path proxy image correction 228 may be accomplished before the other serially, or they may be accomplished simultaneously in a parallel fashion; there is no requirement that the proxy image correction 228 be completed in advance of the primary path image space reconstruction 230.

In one embodiment the copy processor 218 rebins the list mode PET detector space data 212 for additive and multiplicative error correction, for creation of proxy correction data 228 by a secondary histogram reconstructor 226. Multiplicative and additive error correction is accomplished through histogram-based reconstruction techniques, such as for example through the MLEM algorithm process described above, as applied not to each individual event of the plurality of events comprising the PET event dataset 212 on an event-by-event basis, but instead as applied to rebinned sinograms of the PET event dataset 212. In general rebinning event-based data into sinogram reduces the amount of data required to be processed during reconstruction, thus simplifying and providing time efficiencies relative to list-mode reconstruction techniques. A histogram image additive error correction evaluation should differ only marginally from a finer list-based image additive error correction evaluation, even though histogram image reconstruction of the rebinned data is of a lower resolution and is "coarser" than a list processing image reconstruction from the full event-by-event list mode data set 212.

The secondary histogram reconstructor 226 optionally generates a surrogate or proxy image space reconstruction 236 corrected for both multiplicative and additive errors. Optionally the histogram-derived image 236 may be generated for viewing, interpretation or other application; it may be of relatively coarser or lower resolution than the image produced by the list mode reconstructor 230 and would not include TOF information.

As is well known in the art, histogram-based reconstruction is typically faster than event-based list processing reconstruction: accordingly, additive error correction may thus be made available by the faster secondary histogram path 226/228 in advance of the completion of the initial image reconstruction by the primary list mode reconstructor 230. Although configuring the primary path 224/230 to handle all error corrections at the event detection level, including additive errors, would result in the highest degree of image reconstruction accuracy, the difference in processing speed between list processors and histogram processors, commonly on the order of a factor of 10, would result in significantly longer image reconstruction times. By instead utilizing parallel path processing, with a primary event-based list processing path combined with a secondary path for providing additive error information at the image space level, the present embodiment affords faster processing time advantages.

An image correction processor 232 applies the proxy correction data 228 to image data generated by the list-mode reconstructor 230 to generate a final corrected event-based human-readable image 234 for display and use (for example, for display on a computer monitor or other display device). More particularly, the correction is performed in image space. For example, in one embodiment the proxy correction data 228 provides PET image space voxel correction factors, wherein each voxel has a parameter representing the contribution of scatters; another parameter representing the contributions of randoms; and additional parameters, one for each additional additive error correction contemplated. Each voxel will have a unique set of error correction factors as determined in the secondary image reconstructor 226 histogram image reconstruction. Thus once the plurality of individual list mode events 212, corrected for multiplicative errors (e.g. attenuation, normalization, sensitivity, etc.) are reconstructed in image space as voxels in an initial list mode reconstruction by the list mode reconstructor 230, the image correction processor 232 applies each voxel's additive error correction factor(s) from the proxy image correction data 228 to responsively generate the final corrected event-based image 234.

It is to be understood that the present invention is not restricted to the primary list processing/secondary histogram processing embodiment described thus far. In another embodiment the secondary path reconstructor 226 is instead a list processor: in this embodiment the copy processor 218 provides not binned histogram data but a subset of the complete list-mode data 212 to the secondary path list reconstructor 226. For example, every 10th event may be selected and provided to the secondary path processor 226; however, one skilled in the art will recognize that the specific subset size is not critical, and other subset sizes or selection methods may be utilized, optionally selected responsive to performance requirements. In any case, the number of events are preferably selected so that the secondary 226/228 path reconstruction is completed and the proxy image correction information 228 is available before it is needed by the image correction processor 232. Thus the secondary path reconstructor 226 and primary list processor 224 may have equivalent processing speed and/or resource characteristics, with the faster overall speed of the secondary path 226/228 derived from its fractional data set size relative to the complete PET detector event list 212.

Alternative embodiments may even incorporate secondary path 226/228 processors having slower processing speed and/or greater resource characteristics relative to the primary path 224/230, if the disparity in data size or compositions nevertheless enables the secondary path 226/228 to generate the proxy correction information 228 prior to the completion of the primary path 224/230 image space reconstruction. Accordingly, some embodiments may utilize list processing of event data 212 without TOF data in the primary path 224/230, and list processing of a sub-set of the same event data 212 including the TOF data for the secondary path 226/228 for additive error correction and proxy correction 228 derivation.

Where list processing is utilized instead of histogram processing for the secondary path 226/228, an alternative form of additive error correction more appropriate for list processing will be utilized rather than the histogram additive error correction equations described thus far, and suitable error correction procedures will be apparent one skilled in the art.

Figure 2:
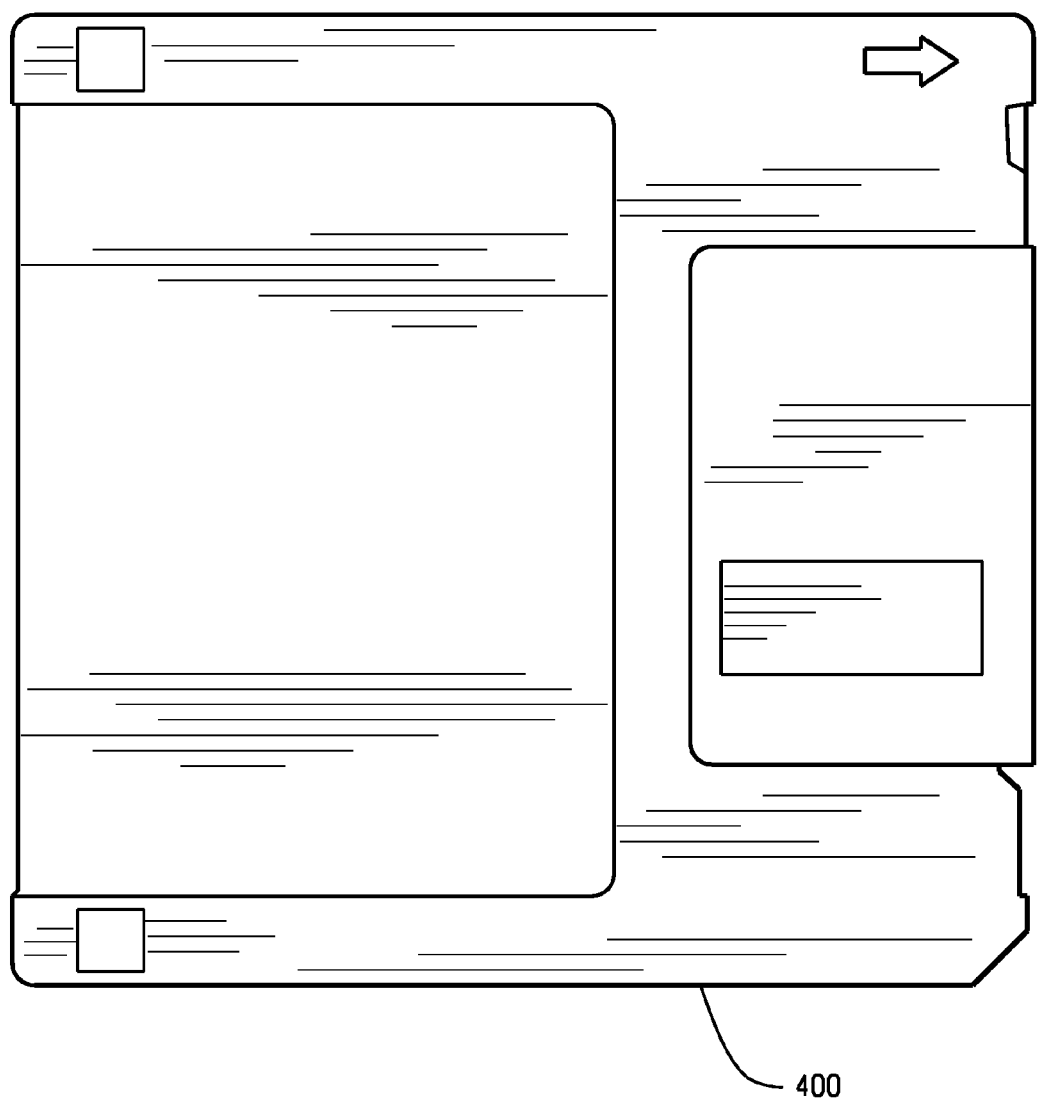
FIG. 2 is a plan view of a computer-readable medium or carrier comprising an embodiment of the present invention tangibly embodied in a computer program residing thereon.

FIG. 2 shows an embodiment of the invention described above tangibly embodied in a computer program residing on a computer-readable medium or carrier 400. Other appropriate machine readable storage mediums include fixed hard drives, optical discs, magnetic tapes, semiconductor memories, such as read-only memories (ROMs), programmable (PROMs), etc. The medium 400 containing the computer readable code is utilized by executing the code directly from the storage device, or by copying the code from one storage device to another storage device, or by transmitting the code on a network for remote execution. The medium 400 may comprise one or more of a fixed and/or removable data storage device such as a floppy disk or a CD-ROM, or it may consist of some other type of data storage or data communications device. The computer program may be loaded into the memory of a computer to configure a processor for execution of the techniques described above. The computer program comprises instructions which, when read and executed by a processor causes the processor to perform the steps necessary to execute the steps or elements of the present invention.

While embodiments of the invention have been described herein, variations in the design may be made, and such variations may be apparent to those skilled in the art of positron imaging, coincidence detection and emission tomography systems and methods, as well as to those skilled in other arts. It will be readily apparent that the techniques described above may be practiced by single, multiple or networked computers. Also a given processor may serve as more than one processor element described above: for example, one processor may serve as two or more of the copy processor 218, list processor 224, secondary reconstructor 226, primary reconstructor 230, or image correcting processor 232 elements described above. The present invention is by no means limited to the specific embodiments and reconstruction processes illustrated above, and other embodiments and reconstruction process implementations will be readily apparent to one skilled in the art. The scope of the invention, therefore, is only to be limited by the following claims and the equivalent thereof.

The invention claimed is:

1. A method, comprising the steps of:
    receiving a plurality of positron annihilation events detected during a positron emission tomography scan;
    reconstructing the plurality of events with a list mode reconstruction technique to generate first tomographic data;
    rebinning the plurality of detected annihilation events to generate rebinned data;
    reconstructing the plurality of events using a second reconstruction technique to generate second tomographic data, wherein the step of reconstructing the events using the second reconstruction technique to generate the second tomographic data comprises reconstructing the rebinned data;
    using the second tomographic data to determine an error correction;
    applying the error correction to the first tomographic data to generate corrected tomographic data; and
    generating an image indicative of the corrected tomographic data.

2. The method of claim 1 wherein the step of reconstructing the events using the second reconstruction technique to generate the second tomographic data comprises using a using a list-based reconstruction technique to reconstruct a subset of the plurality of detected positron annihilation events.

3. The method of claim 1 wherein the second tomographic data has a lower spatial resolution than a spatial resolution of the first tomographic data.

4. The method of claim 1 wherein the steps of reconstructing the events using the list-based reconstruction technique to generate the first tomographic data and reconstructing the events using the second reconstruction technique to generate the second tomographic data are performed temporally in parallel.

5. The method of claim 1 further comprising the step of performing a multiplicative error correction on the plurality of detected positron annihilation events to generate a corrected plurality of events; wherein the step of reconstructing the events using the list-based reconstruction technique to generate the first tomographic data comprises reconstructing the corrected plurality of events; and wherein the step of using the second tomographic data to determine an error correction comprises determining an additive error correction, the additive error correction including at least one of scatter and randoms.

6. The method of claim 5 wherein the multiplicative corrections include at least one of scanner dependent corrections and patient-specific corrections.

7. The method of claim 5, further comprising the step of using tomographic data from a CT scan to generate an attenuation map, wherein the step of performing multiplicative error correction includes using the generated attenuation map.

8. The method of claim 1, wherein at least one of the steps of reconstructing the events using a list-based reconstruction technique and reconstructing the events using a second reconstruction technique further comprises the step of generating tomographic data responsive to event time of flight data.

9. A method, comprising the steps of:
    performing a multiplicative error correction on each of a plurality of positron annihilation events detected during a positron emission tomography scan to generate a plurality of corrected events, the plurality of detected annihilation events and the plurality of corrected events including time of flight data, wherein performing multiplicative error correction includes using an attenuation map generated from a different modality;
    reconstructing the corrected events using a list-based reconstruction technique to generate first tomographic data;
    rebinning the plurality of detected annihilation events to generate rebinned data;
    reconstructing the rebinned data by a histogram-based reconstruction technique to generate second tomographic data corrected for additive and multiplicative errors;
    using the second tomographic data to determine an additive-error correction; applying the additive-error correction to the first tomographic data to generate corrected tomographic data; and
    generating an image indicative of the corrected tomographic data; wherein the additive corrections include at least one of scatter and randoms, and the multiplicative corrections include at least one of scanner dependent corrections and patient-specific corrections.

10. An apparatus, comprising:
    a list-mode first reconstructor means for reconstructing a plurality of positron annihilation events detected during a positron emission tomography scan to generate first data;
    a rebinning means for rebinning the plurality of detected annihilation events to generate rebinned data;
    a second reconstructor means for reconstructing the plurality of positron annihilation events to generate second data, wherein the second data is used to determine an error correction, wherein the second reconstructor means reconstructs the rebinned data to generate the second data;
    an image correction processor means for applying the error correction to the first data to generate corrected data; and a display means for generating an image indicative of the corrected data.

11. The apparatus of claim 10 wherein the second reconstructor means is a list-based reconstructor means configured to reconstruct a subset of the plurality of detected positron annihilation events to generate the second data.

12. The apparatus of claim 10, the first reconstructor means further configured to perform a multiplicative error correction on the plurality of positron annihilation events to generate a corrected plurality of events and generate the first data from the corrected plurality of events; wherein the error correction determined from the second data comprises an additive error correction including at least one of scatter and randoms.

13. An article of manufacture comprising a non-transitory computer usable medium having a computer readable program embodied in said medium, wherein the computer readable program, when executed on a computer, causes the computer to:
   reconstruct a plurality of positron annihilation events detected during a positron emission tomography scan with a list-mode reconstruction technique to generate first data;
   rebin the plurality of detected annihilation events to generate rebinned data:
   reconstruct the plurality of positron annihilation events to generate second data by reconstructing the rebinned data:
   use the second data to determine an error correction;
   apply the error correction to the first data to generate corrected data; and
   generate an image indicative of the corrected data.

14. The article of manufacture of claim 13, wherein the computer readable program, when executed on the computer, causes the computer to reconstruct the detected annihilation events by using a using a list-based reconstruction technique to reconstruct a subset of the plurality of detected positron annihilation events.

15. The article of manufacture of claim 13, wherein the computer readable program, when executed on the computer, causes the computer to perform at least one of reconstructing the events using a list-based reconstruction technique and reconstructing the events using a second reconstruction technique responsive to event time of flight data.

16. The article of manufacture of claim 13, wherein the computer readable program, when executed on the computer, causes the computer to perform a multiplicative error correction on the plurality of positron annihilation events to generate a corrected plurality of events; wherein the computer reconstructs the events using the list-based reconstruction technique to generate the first data by reconstructing the corrected plurality of events; and wherein the computer uses the second data to determine an error correction comprising an additive error correction, the additive error correction including at least one of scatter and randoms.

17. A system, comprising:
   a first processor means for performing a first error correction to a plurality of positron annihilation events detected during a positron emission tomography scan to generate first corrected event data;
   a first reconstructor means for reconstructing the first corrected event data to generate first volumetric data;
   a second processor means for rebinning the plurality of detected annihilation events to generate rebinned data, wherein the a-second processor means performs a second error correction to at least a subset of the rebinned data to generate second corrected event data;
   a second reconstructor means for reconstructing the second corrected event data to generate an error correction;
   an image correction processor means for applying the error correction to the first volumetric data to generate corrected volumetric data; and
   a display means for generating a human-readable image indicative of the corrected volumetric data; wherein the second processor means and the second reconstructor means define a second reconstruction path configured to generate the error correction before a first reconstruction path defined by the first processor means and the first reconstructor means generates the first volumetric data.

18. The system of claim 17 wherein the second processor means is a list-based processor; and the second reconstructor means is a list-based reconstructor.

* * * * *